United States Patent [19]

Halford et al.

[11] 4,401,130
[45] Aug. 30, 1983

[54] SWAB ARTICLE

[75] Inventors: George C. Halford, Chardon; John E. Goodrich, Mentor, both of Ohio

[73] Assignee: Halbrand, Inc., Willoughby, Ohio

[21] Appl. No.: 876,464

[22] Filed: Feb. 9, 1978

[51] Int. Cl.³ .............................................. A45D 40/30
[52] U.S. Cl. .................................................... 132/88.5
[58] Field of Search ....................... 132/88.5, 88.7, 89, 132/90, 93; 128/304, 221–223; 30/316, 280

[56]  References Cited
U.S. PATENT DOCUMENTS 1,557,464 10/1925 Mick ................................ 30/316 X
2,570,596 10/1951 Ross ................................... 15/140.3
3,078,856 2/1963 Bender et al. ......................... 132/93
3,640,268 2/1972 Davis ................................... 128/304
4,010,543 3/1977 Nusbaum .............................. 30/316

Primary Examiner—Gregory E. McNeill
Attorney, Agent, or Firm—Frank B. Robb

[57]  ABSTRACT

There is disclosed a swab article having a polyester urethane foam body of any preferred form fastened to a handle extending into a bore in said body, which bore is created without dust and in which the handle is maintained by adhesive, the bore in the body having a cushioned bottom to prevent the handle from penetrating therethrough during use.

9 Claims, 8 Drawing Figures

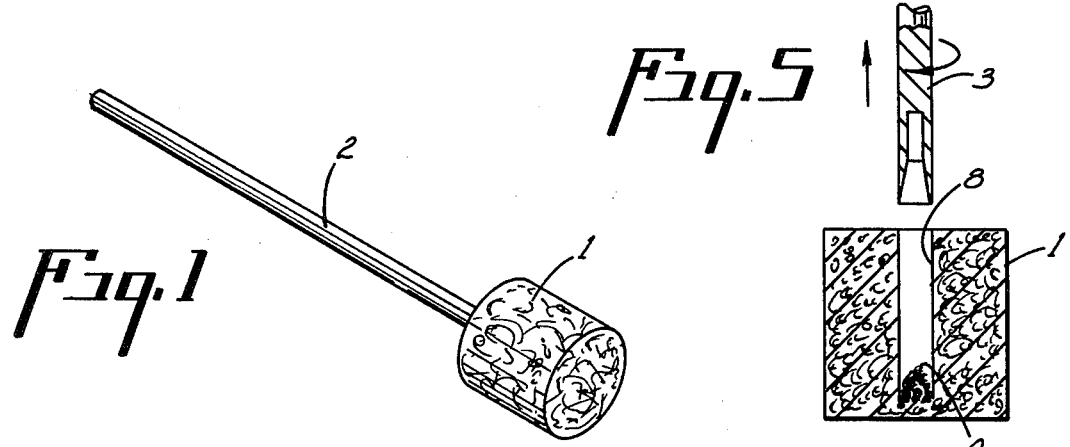
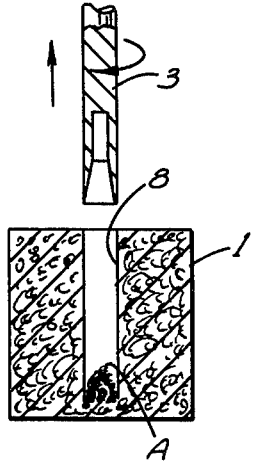
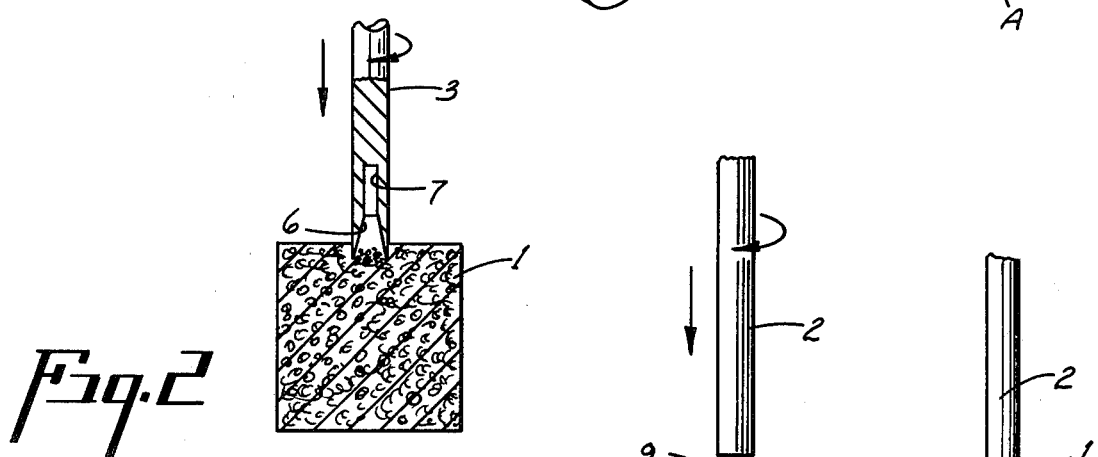
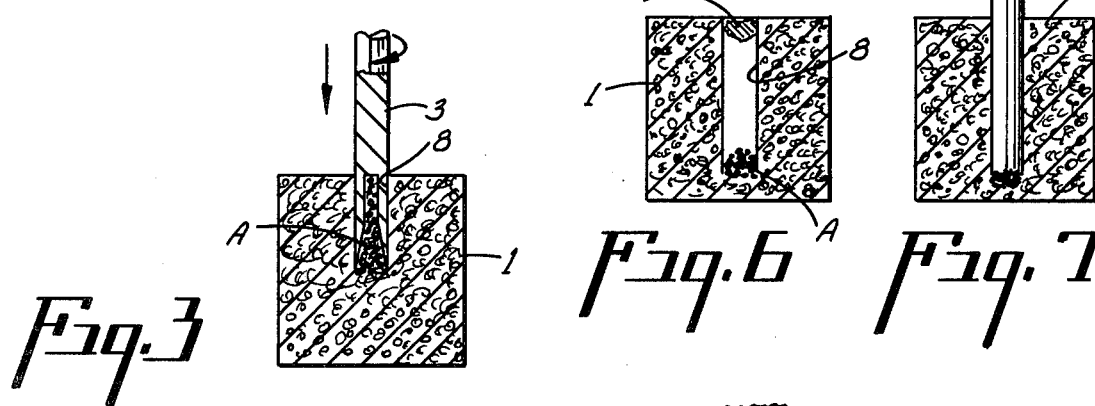
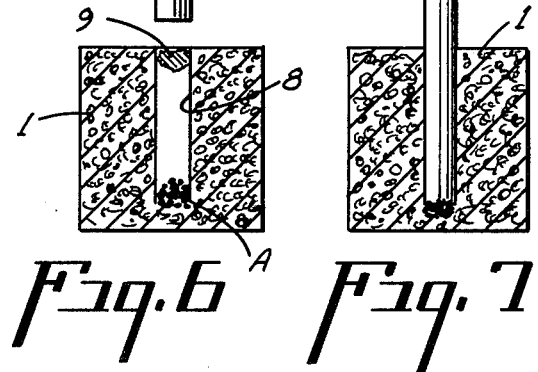
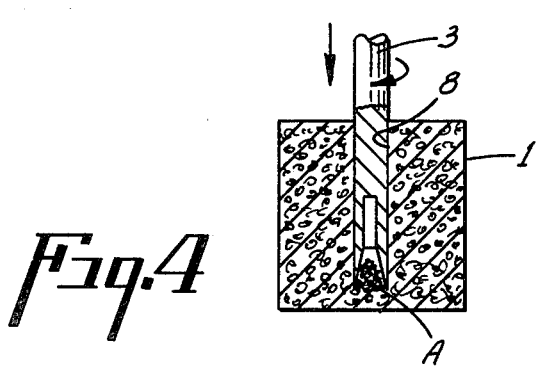
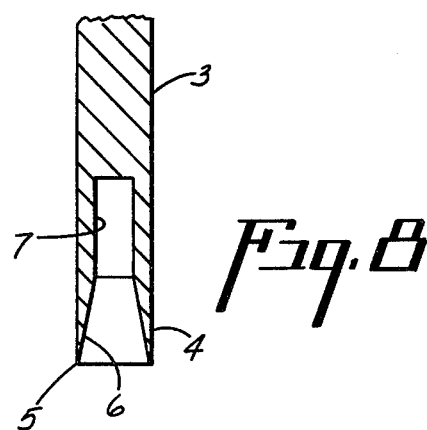

SWAB ARTICLE

BACKGROUND OF THE INVENTION

While the article of the instant invention superficially appears to resemble the combination toothbrush and pick of U.S. Pat. No. 3,646,628, and does in fact comprise a body somewhat like that patent and a handle member of similar composition, such article being suitable for similar use, as a matter of fact the instant article is quite different and useful for other purposes, primarily that of a swab where such use is desirable and suitable, sanitary considerations being important and elimination of dust and foreign particles being essential.

Whereas the body of the swab hereof, is of the same composition and of generally comparable size, it is basically different in its relation with the handle and the cushioning provided by the novel manner in which the swab body is prepared to receive the handle. Such preparation and positioning is specifically arranged to prevent the end of the handle from protruding from the body whereas the structure of the U.S. Pat. No. 3,646,628 is availed of to facilitate the sharpened end of the handle thereof to be extended beyond the end of that body to perform its intended function.

OBJECTS OF THE INVENTION

With the foregoing in mind it is an object of this invention to provide a swab article comprising a body of synthetic foam material having an elongated handle receiving bore therein with cushioning means at the bottom of said bore which is formed at the same time as the bore.

Another object of the invention is to form the bore by severing material therein and twisting said material in a manner to densify the material and at the same time position the same at the bottom of the bore.

Yet a further object of the invention is to create a bore in a swab body with cushioning means at its bottom, and to fasten a handle therein by initially depositing a quantity of adhesive filling the entrance to the bore, and inserting the end of the handle to cause the adhesive to be distributed along the interior of the bore to thereby retain the handle in connection with the swab.

Still another object of the invention is to form the bore in the swab body with a tool to sever material of the body without creating dust or fine particles of material and twisting the material in such a manner as to cause the same to assume a position at the bottom of the bore and facilitate the removal of the tool without disturbing such thus positioned material.

Other and further objects of the invention will be understood from a consideration of the specification appended hereto and disclosed in the drawing wherein:

FIG. 1 is a perspective view of the swab article of this invention.

FIG. 2 is to illustrate in that and successive figures, the method of creating the bore in the swab article body, as by introducing a suitable tool thereinto and following the specific positions of FIGS. 2, 3 and 4 causing the tool to enter the body and move to the lower extremity thereof.

FIG. 5 shows the tool as removed from the body having performed its boring function.

FIG. 6 illustrates a handle positioned prior to insertion into the body and with the adhesive in position.

FIG. 7 discloses the body and handle in connected relationship.

FIG. 8 illustrates an enlarged detail, somewhat fragmentary, the boring tool availed of to perform the boring operation.

DESCRIPTION OF THE INVENTION

Although it might seem simple to bore a hole in a foam body and insert a handle with adhesive on the end, in such bore, in practice it has been found difficult to produce a safe, sanitary article such as is hereby provided.

The material described as expanded polyester urethane foam of 50 to 80 pore, and having a density of about two (2) pounds per cubic foot, of which the swab article of this invention is made, has been found to be particularly advantageous because of many properties which it has, including absorption, and ability to maintain in sanitized condition among others.

However, certain problems are involved in the manufacture of articles such as the swab hereof, including the machining of holes as necessary in the bodies to receive the ends of the handles. Known tools customarily produce substantial quantities of fine dust retained in the pores, and some non-uniformity of the bore, both of which are objectionable, the dust being completely unacceptable as being possibly dangerous when open wounds are subject to treatment using the swabs.

The non-uniformity of holes bored by other means, results in poor handle adhesion and also may create problems, when the parts become separated.

Thus the substantially improved articles provided by practice of this invention which eliminates those problems will be readily understood and the method of manufacture and tool provided, improve acceptance and other attributes.

Further since this swab is intended to be used in a sanitary manner and for swab purposes, it is obvious that such impurities or the lack of sanitary aspects cannot be tolerated in an article of this kind and thus it is not only necessary but desirable to provide the article without such attendant difficulties or undesired qualities.

Further although it is possible a small cushion of material could be inserted in the bore in which the handle is positioned, it is not practical from a cost standpoint since a disposable swab of the kind here contemplated must be provided on a very cost competitive basis and it is distinctly desirable not to permit the handle to penetrate through the swab and extend beyond the end of the body thereof so as to possible irritate and otherwise endanger a patient with which the swab is associated as a swabbing article.

In addition, even the dipping of a handle end in an adhesive which would dry rapidly enough to be useful, is accompanied by many problems not the least of which is premature drying, but even the act of inserting the end of the handle in the bore usually results in wiping adhesive off at the bore entrance and poor adhesion.

Having the foregoing in mind, the article of this invention is disclosed in FIG. 1, as comprising a body of generally cylindrical formation designated 1, relatively small in diameter and short in extent, from which extends a handle 2, the body in this case being made of polyester urethane foam or other expanded material and relatively soft in composition, similar or possibly identical in fact to that of the patent previously referred to, with a handle 2 of like composition to that of the patent and adhered to the body to fasten the same permanently together.

In order to provide the article hereinbefore referred to, a novel concept has been developed, involving a tool which is illustrated in FIG. 8 in enlarged detail, which comprises a cylindrical tool body 3, having a hollow end 4, the hollow end being formed with an extremely sharp lower edge 5, which in turn is created by tapering inwardly the surface 6, and which extends to a cylindrical portion 7 extending into the tool body 3.

It should be borne in mind that this tool 3 is of very small diameter, and thus the opening provided therein to form the sharpened lower edge is somewhat critical and difficult to provide.

Suffice to say it has been provided and is used to form the bore herein by following the steps illustrated in FIGS. 2 to 4 inclusive, which involves the positioning of the body 1 so that the tool 3 may penetrate the same, the tool 3 being rotated at a speed of 5000 RPM, preferably and desirably as has been ascertained from use, to thereby assume the position of FIG. 2.

Subsequent downward movement of the tool 3 in its rotational operation, will sever the material in the bore designated 8 in the body 1, gathering the said material inwardly of the tool in the opening formed by the surface 6 and portion 7.

As the tool is caused to penetrate into position of FIG. 4, rotation being maintained, the material is further gathered into the interior of the tool, and compressed therein likewise.

Interestingly enough, it has been found that the tool not only severs the material from the bore, but at the same time twists and compresses the same, the interior of the tool having a much smaller volumetric capacity than the actual bore itself.

As the tool continues to be rotated it is thereafter withdrawn as in FIG. 5, leaving the severed material at the bottom of the body 1, this material now being designated A, and being not only compressed and twisted but retaining its position substantially entirely at the bottom of the bore 7 though connected at its end to the body.

Thereafter, a suitable quantity of adhesive designated 9, as shown in FIG. 6, is positioned at the mouth of the bore 8, and as such by reason of its characteristics retained at said bore entrance, until the stick or handle 2 is inserted thereinto.

At this time the adhesive 9 is caused to move downwardly along the walls of bore 8 and over the exterior surface of the handle 2, the handle finally assuming the position shown in FIG. 7 in full engagement with the body 1 and bore 8 therein.

It should be observed that the mass of twisted compressed material at the bottom of the bore is now serving to cushion the area around the bottom of the bore and to prevent the handle 2 from penetrating through the material of the body into a position where it might damage or otherwise engage tissue surfaces or the like and irritate the same.

It is thus seen that the combination hereof, involving a foam body and handle is formed in such a manner as to positively maintain the two in connection, and yet provide a cushioned area at the end to prevent penetration of the handle through the body, permitting its use for swabbing or like purposes.

We claim:

1. The method of forming a bore having a cushioned bottom in a polyester foam body which comprises, rotating and penetrating into the body, a hollow interior boring tool having a cylindrical exterior surface and a sharp edge extremity formed by an inwardly tapered section extending into the hollow interior, whereby to sever the material from the body to form a cylindrical bore whilst the severed material remains connected to the body in advance of said edge, gathering the material severed inwardly into the interior aforesaid and twisting the material as the bore is formed, the severed material remaining connected to the body.

2. The method of forming a bore having a cushioned bottom in a polyester foam body which comprises, rotating and penetrating into the body, a hollow interior boring tool having a cylindrical exterior surface and a sharp edge extremity formed by an inwardly tapered section extending into the hollow interior, whereby to sever the material from the body to form a cylindrical bore whilst the material remains connected to the body in advance of said edge, gathering the material severed inwardly into the interior aforesaid and twisting the material as the bore is formed and thereafter withdrawing the tool during rotation thereof, the severed material remaining connected to the body at the lower end of said material.

3. The method of claim 1, wherein the gathering and twisting of the severed material causes the same to be compressed in proportion to the diameter and depth of the interior of the tool.

4. The method of claim 1, wherein the severed material is compressed into the interior of the tool and twisted whilst connection of the severed material is maintained beyond the point of severance.

5. The method of claim 2, wherein the tool is rotated at a speed in the order of 5000 RPM, during its severing and withdrawal operation.

6. An article as claimed in claim 1, wherein the cushioning means comprises material severed from the body during formation of the bore.

7. An article as claimed in claim 6, wherein the material is twisted and compressed and positioned at the bottom of the bore.

8. An article as claimed in claim 7, wherein the cushioning means is integrally connected to the bottom of the bore.

9. An article as claimed in claim 7, wherein the cushioning means comprises material severed from the body without creating dust during formation of the bore, and such material is twisted and compressed.

* * * * *